United States Patent [19]

Heitkämper et al.

[11] Patent Number: 4,480,110
[45] Date of Patent: Oct. 30, 1984

[54] PROCESS FOR THE PREPARATION OF URETHANES

[75] Inventors: Peter Heitkämper, Dormagen; Rudolf Fauss, Cologne; Kurt Findeisen, Odenthal; Stefan Penninger, Dormagen; Hans-Joachim Scholl, Colonge, all of Fed. Rep. of Germany

[73] Assignee: Bayer Aktiengesellschaft, Leverkusen, Fed. Rep. of Germany

[21] Appl. No.: 569,533

[22] Filed: Jan. 9, 1984

Related U.S. Application Data

[63] Continuation of Ser. No. 197,041, Oct. 15, 1980.

[30] Foreign Application Priority Data

Oct. 27, 1979 [DE] Fed. Rep. of Germany ....... 2943550

[51] Int. Cl.$^3$ ............................................. C07C 125/06
[52] U.S. Cl. ........................................ 549/467; 560/9; 560/12; 560/13; 560/24; 560/25; 560/115; 560/135; 560/148; 560/150; 560/156; 560/158; 560/157

[58] Field of Search ................... 560/24, 25, 157, 158, 560/115, 148, 156, 135, 150, 9, 12, 13; 549/467

[56] References Cited

U.S. PATENT DOCUMENTS 2,409,712 10/1946 Schweitzer et al. ................. 260/453
2,806,051 9/1957 Brockway ............................ 560/24
2,834,799 5/1958 Sowa ..................................... 560/24

OTHER PUBLICATIONS

Paquin, Chem. Abs., 42 (1948) 123(i).

*Primary Examiner*—Bernard Helfin
*Attorney, Agent, or Firm*—Gene Harsh; Joseph C. Gil; Lyndanne M. Whalen

[57] ABSTRACT

A process for the preparation of N,O-disubstituted urethanes. A substituted urea, an alcohol and a compound taken from the group consisting of N-unsubstituted urethanes, urea, polyurets and mixtures thereof at a temperature of 120°–350° C. The urethanes prepared by this process are particularly suitable for the preparation of isocyanates.

5 Claims, No Drawings

PROCESS FOR THE PREPARATION OF URETHANES

This application is a continuation of application Ser. No. 197,041, filed Oct. 15, 1980.

BACKGROUND OF THE INVENTION

This invention relates to an improved process for the production of N,O-disubstituted urethanes by reacting substituted ureas with alcohols. The products obtained by this process are particularly useful in the production of the isocyanates on which they are based.

It is known that urethanes may be formed by reacting organic isocyanates with alcohols. This reaction is reversible, i.e., urethanes may be thermally split into the isocyanate and the alcohol on which they are based (see, for example, U.S. Pat. No. 2,409,712). Urethanes which may be thermally split into isocyanates are, therefore, potential starting materials for the production of such isocyanates.

Isocyanates are commercially produced to a very large extent by reacting primary amines with phosgene. The production of urethanes without phosgene and the subsequent thermal splitting thereof would be an interesting alternative to this commercially used method. One method of producing urethanes without the use of phosgene which has been explored is a reaction of substituted ureas with alcohols in a manner such as that described in U.S. Pat. Nos. 2,409,712. However, this known method produces insufficient amounts of the urethane for commercial purposes. The inadequate yields obtained from the procedure of U.S. Pat. No. 2,409,712 are attributable to the fact that the primary amine corresponding to the urea substituent forms as a secondary product.

SUMMARY OF THE INVENTION

It is an object of the present invention to provide an improved process for the production of N,O-disubstituted urethanes by reacting substituted ureas with alcohols in such a way that the formation of undesirable secondary products, particularly primary amines, is largely avoided.

It is a further object of this invention to provide a process for the production of N,O-disubstituted urethanes in commercially significant amounts of reacting substituted areas with alcohols.

These and other objects which will be apparent to those in the art may be achieved by simultaneously reacting: (a) substituted ureas with (b) alcohols and at least one compound taken from the group consisting of N-unsubstituted urethanes, ureas and mixtures thereof at temperatures of from 120° to 350° C.

The process according to the present invention is particularly suitable for the preparation of urethanes corresponding to the following general formula:

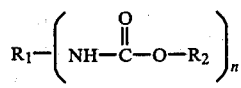

wherein
$R_1$ represents an optionally substituted aliphatic hydrocarbon radical containing from 1 to 18 carbon atoms, an optionally substituted cycloaliphatic hydrocarbon radical containing from 3 to 18 carbon atoms, an optionally substituted aromatic hydrocarbon radical containing from 6 to 15 carbon atoms, an optionally substituted araliphatic hydrocarbon radical containing from 7 to 14 carbon atoms or an optionally substituted 5- or 6-membered heterocyclic radical which may be fused with a benzene ring,
$R_2$ represents an optionally substituted alkyl radical containing from 1 to 20 carbon atoms, an optionally substituted cycloalkyl radical containing from 3 to 16 carbon atoms or an optionally substituted aralkyl radical containing from 7 to 14 carbon atoms, and
n represents an integer of from 1 to 3.

Where the n in the formula represents 2 or 3, at least 2 carbon atoms should be present between the urethane groups attached to the radical $R_1$.

Substituents for the aliphatic or cycloaliphatic radicals $R_1$ and $R_2$ include $C_6$-$C_{10}$ aroxy, $C_1$-$C_6$ alkoxy, $C_1$-$C_6$ alkoxy-$C_2$-$C_4$ alkoxy, $C_1$-$C_6$ acyl, $C_1$-$C_6$ alkyl mercapto, $C_6$-$C_{10}$ aryl mercapto, $C_1$-$C_{12}$ alkyl carbonyl, bis-($C_1$-$C_8$ alkyl)-amino, $C_1$-$C_6$ acyl amino, nitro, cyano or thiocyano radicals.

Suitable substituents for the aromatic or araliphatic radicals $R_1$ and $R_2$ include $C_1$-$C_{12}$ alkyl, $C_1$-$C_{12}$ alkyl sulfonyl, $C_6$-$C_{10}$ aryl sulfonyl, $C_1$-$C_{12}$ alkyl sulfonic acid ester or sulfonamide radicals.

It is preferred, however, that
$R_1$ represent an aliphatic hydrocarbon radical containing from 3 to 18 carbon atoms, a cycloaliphatic hydrocarbon radical containing 6 to 15 carbon atoms or an optionally methyl-, methoxy- or chlorine-substituted $C_6$-$C_{15}$ hydrocarbon radical optionally containing methylene bridges,
$R_2$ represent a $C_1$-$C_4$ alkoxy- or $C_1$-$C_4$ alkoxy $C_2$-$C_4$ alkoxy-substituted or unsubstituted aliphatic hydrocarbon radical containing from 1 to 18, (most preferably 1 to 4) carbon atoms, of the type obtained by removing the hydroxyl group from a monohydric unsubstituted primary or secondary aliphatic alcohol, or a cyclohexyl or 2-phenyl ethyl radical, and
n represent 1 or 2.

DESCRIPTION OF THE PREFERRED EMBODIMENTS

The urethanes of the present invention are prepared by reacting a substituted urea, an alcohol and at least one compound taken from the group consisting of N-unsubstituted urethanes, ureas, polyurets and mixtures thereof at 120°-350° C. Substituted ureas which may be used in the present invention include: N-monosubstituted, N,N'-disubstituted ureas or linear polyureas. It is preferred that the N-monosubstituted and N,N'-disubstituted ureas contain terminal urethane or amino groups. The preferred linear polyureas have a maximum molecular weight of 2,000, with the most preferred being those having a maximum molecular weight of 700. The urea, urethane and amino groups of these materials should be attached to one another through hydrocarbon radicals. Preferably, the urea groups are substituted with hydrocarbon radicals which correspond to $R_1$ as defined for the general formula given above. It is also preferred that terminal urethane groups, if any, be substituted on the oxygen atom with a substituent corresponding to the definition of $R_2$, given above. The total content of urea groups (—NH—CO—NH—) and urethane groups (—NH—CO—O—) corresponds to a content of the structural unit (—NH—CO—) of from 5 to 58%, preferably from 10 to 58%, by weight.

Typical examples of suitable substituted ureas include: methyl-, ethyl-, isobutyl-, octadecyl-, phenyl-, cyclohexyl-, or benzyl-urea, N,N'-dimethylurea, N,N'-diisobutyl-urea, N,N'-diphenyl-urea, N,N'-(3,3'-didibenzofuranyl)-urea, N,N'-di-(4-chlorophenyl)-urea, N,N'-di-(4-methoxy phenyl)-urea, N,N'-dicyclohexyl-urea and compounds corresponding to the following general formulae:

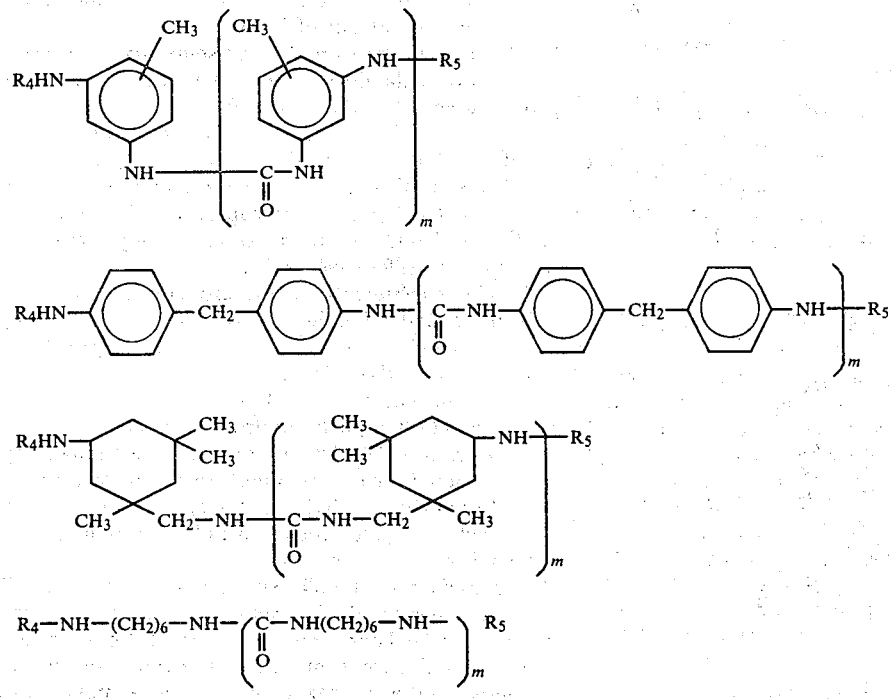

wherein
m represents an integer or a number (in the case of statistical mixtures) of from 1 to 10,
$R_4$ and $R_5$, which may be the same or different, represent H, $COOR_2$, $COHN_2$ or $COHNR_6$, wherein $R_6$ represents a monofunctional radical of the type mentioned in the definition of $R_1$.

The unsubstituted ureas which may be used in the present invention include the ureas prepared in accordance with procedures standard in the art. Suitable procedures include those described in D. F. Kutepow, Russ, Chem. Rev. 31, 633 (1962) and H. Rinke, Houben-Weyl XIV/2, 165 et seq. Substituted ureas suitable for use in the present invention include the compounds obtained as secondary products in the synthesis of urethanes from urea, amine and alcohol by the processes disclosed in U.S. Pat. Nos. 2,409,712 and 2,806,051, herein incorporated by reference. N,N'-disubstituted monoureas and the bis-ureas are preferably used.

Alcohols which may be used in making the urethanes of the present invention correspond to the general formula, $R_2$—OH wherein $R_2$ is as defined above. Examples of suitable alcohols include: methanol; ethanol; propanol; i-propanol; butanol; i-butanol; pentanol; i-pentanol; hexanol; i-hexanol; heptanol; i-heptanol; octanol; i-octanol; nonanol; i-nonanol; decanol; i-decanol; dodecanol; 2-ethyl hexanol; β-chloroethanol; 2-ethyl butanol; hexadecanol; octadecanol; fatty alcohol mixtures; 2-methoxy ethanol; 2-ethoxy ethanol; 2-propoxy ethanol; 2-butoxy ethanol; 2-(2-methoxy ethoxy)-ethanol; 2-(2-ethoxy ethoxy)-ethanol; 2-(2-butoxy ethoxy)-ethanol; cyclopentanol; cyclohexanol; methyl cyclohexanol (and mixtures); cyclohexamethanol; 3,3,5-trimethyl cyclohexanol; 4-t-butyl cyclohexanol; 2-hydroxy decalin; borneol; i-borneal; 1-(2-hydroxy ethoxy)-4-nitrobenzene; benzyl alcohol; 2-phenyl ethanol; 2-(methoxy phenoxy)-ethanol (and mixtures); 1-phenyl ethanol; 3-phenyl-1-propanol and 4-methoxy benzyl alcohol. Particularly preferred alcohols include: methanol; ethanol; n-propanol; i-propanol; n-butanol; i-butanol; cyclohexanol; n-hexanol; 2-ethyl hexanol; β-phenyl ethanol; glycol monomethyl ether; glycol monobutyl ether or diglycol monomethyl ether.

The N-unsubstituted urethanes which may be used in the present invention correspond to the general formula:

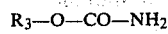

$$R_3-O-CO-NH_2$$

wherein $R_3$ represents an optionally chlorine- or $C_1$-$C_4$ alkyl-substituted aromatic hydrocarbon radical containing a total of from 6 to 15 carbon atoms or one of the radicals corresponding to the definition of $R_2$ given above.

Typical examples of suitable N-unsubstituted urethanes include: methyl, ethyl, n-propyl, i-propyl, n-butyl, i-butyl, cyclohexyl or benzyl carbamate, the N-unsubstituted urethanes derived from the alcohols exemplified above or even phenyl-4-chlorophenyl, 4-methyl phenyl or 1-naphthyl carbonate.

Urea or polyurets, particularly biuret, triuret or tetrauret or mixtures thereof may also be used in the practice of the present invention.

In the practial application of the process according to the present invention, the alcohol component should be used in an at least stoichiometric quantity, based on the number of carbonyl groups forming a urea or urethane group present in the substituted urea, N-unsubstituted urethanes or ureas and/or polyurets used. It is preferable that the reactant alcohol be used in a stoichiometric excess so that the equivalent ratio of hydroxyl groups to carbonyl groups amounts to from 1:1 to 10:1, more preferably from 1:1 to 5:1. In calculating the quantitative ratio, allowance must be made for the alcohol bound in the form of a urethane group of one or more of the other reactants where this bound alcohol corresponds to the reactant alcohol. If the chemically bound alcohols differ from the reactant alcohol and are eliminated during the reaction, the chemically bound alcohol is not included in the calculation of the quantitative ratios.

In the process according to the present invention, the N-unsubstituted urethanes are used in a quantity of from 0 to 300% by weight, preferably from 0 to 150% by weight, based on the substituted ureas. The ureas and/or polyurets are used in a quantity of from 0 to 100% by weight, preferably from 0 to 70% by weight, based on the substituted ureas. The total quantity of N-unsubstituted urethanes, ureas and/or polyurets should amount to at least 10% by weight, preferably at least 15% by weight, based on the quantity of substituted urea.

The process according to the present invention is preferably carried out in the presence of suitable catalysts. Suitable catalysts are compounds which have a catalytic effect on the esterification of carboxylic acids. Catalysts particularly suitable for the process according to the present invention are (i) inorganic or organic bases which are inert under the reaction conditions; (ii) Lewis acids; and (iii) salts and complex compounds, such as chelates, or transition metals.

Examples of suitable catalysts (i) include: tertiary amines such as tri-n-propylamine, triethylamine, triisopentylamine, diethylbenzylamine, N,N-dimethylbenzylamine, hexahydrodimethylaniline, N-ethyl-piperazine, diethyl-(2-methoxy propyl)-amine, 2-(diethyl ammoethyl)-phenyl ether, ethoxyl morpholine, N-(2-diethyl aminoethyl)-benzamide, N-(2-diethylaminoethyl)-propionamide, 1,4-diaza-(2,2,2)-bicyclooctane, N,N-dimethyl-4-aminopyridine, 1-azabicycloheptanes, 1-azabicyclooctanes; saturated polyheterocyclic amines such as 3-methyl conidine, 1-azabicyclo-(3,2,1)-octane, pyrrolizidines and quinuclidines; inorganic bases such as beryllium hydroxide and sodium, potassium, lithium, magnesium, barium or calcium hydroxide; basic alkali metal salts such as sodium carbonate, sodium sulfide, potassium carbonate or trisodium phosphate and also alkali metal salts of fatty acids acids or sulfonic acids.

Suitable catalysts (ii) are, for example, Lewis acids such as iron(II) chloride, iron(III) chloride, zinc chloride, tin(II) chloride, tin(IV) chloride, aluminum chloride, zinc cyanide, boron trifluoride or boron trifluoride etherate.

Suitable catalysts (iii) are, for example, salts of transition metals other than (ii) and complex compounds, particularly chelates of these metals such as cobalt, manganese or lead naphthanates, iron oleates or carbonyls, acetylacetonates or iron, nickel, cobalt, zinc, lead, aluminum, manganese, magnesium, molybdenum, titanium, thorium, zirconium or vanadium, bis-(dibenzoyl methane)-copper, bis-(ethyl acetoacetate)-copper, iron, coordination compounds of titanium, zirconium, hafnium, thorium and manganese with $\beta$-diketones, $\beta$-ketoesters and $\beta$-hydroxy aldehydes, dibutyl tin dilaurate, dibutyl tin diacetate, di-(2-ethyl hexyl)-tin oxide, dioctyl tin oxide, tin salts of $C_1$–$C_{20}$ carboxylic acids such as tin(II) naphthanate, hexoate, calmitate, stearate or dimethyl valerate, acetates, chlorides, sulfates or octoates of divalent or trivalent cobalt, monovalent or divalent copper or divalent lead.

Particularly suitable catalysts are, for example, zinc chloride, zinc acetate, zinc octoate, zinc oxide, zinc cyanide, tin(II) chloride, tin(IV) chloride, dibutyl tin dilaurate, cobalt triacetate, cobalt trichloride, cobalt trioctoate, copper(II) acetate, copper(I) chloride, copper(II) sulfate, lead acetate or lead chloride.

The particular catalyst may be used in a quantity of from 1 ppm to 20% by weight, preferably from 100 ppm to 5% by weight, based on the sum of the starting materials. In practice, every effort should, of course, be made to keep the concentration of the catalysts as low as possible. The optimum catalyst concentration depends upon the type of starting materials used and upon the activity of the particular catalyst and may be readily determined by one skilled in the art.

The process according to the present invention may be carried out under pressure or in the absence of applied pressure. The application of pressure, for example from 1 to 80 bars, is, however, often appropriate when the reaction temperature is above the boiling point of one or more of the starting materials. However, it is also possible to heat a mixture of the substituted ureas with the N-unsubstituted urethanes to the reaction temperature and to add the alcohol even if it has a boiling point which is below the reaction temperature without pressure at such a rate that the alcohol is continuously consumed and the reaction temperature is maintained. If urea and/or polyurets are also used as coreactant it is appropriate to add this component together with the alcohol to the mixture of the substituted ureas with the N-unsubstituted urethanes.

The process according to the present invention is generally carried out at temperatures of from 120° to 350° C., preferably from 130° to 300° C., and most preferably from 140° to 250° C.

The process according to the present invention may be carried out in the presence or absence of solvents. Suitable solvents are, for example, solvents which are inert under the process conditions and which have a boiling point of from 100° to 280° C., preferably from 150° to 250° C. Examples of suitable solvents include: n-nonane; n-butyl cyclohexane; decahydronaphthalene; n-undecane; n-dodecane; n-hexyl cyclohexane; dipentene; 1-dodecene; isopropyl benzene; 1,3-diethyl benzene; indene; n-butyl benzene; tetralin; chlorobenzene; 4-chlorotoluene; 1,2-dichlorobenzene; 2,4-dichlorotoluene; 1,2,4-trichlorobenzene; 2-chloro-4-isopropyl-1-methyl benzene; anisole; cyclohexyl ethyl ether; diethylene glycol dimethyl ether; benzyl methyl ether; 4-methoxy toluene; p-chloroanisole; di-n-hexyl ether; phenyl-n-propyl ketone; benzophenone; acetophenonene; formamide; N,N-dimethyl formamide; N,N-diethyl formamide; N-methyl formamide; dimethyl acetamide; N-methyl pyrrolidone; caprolactam; phenol; substituted phenols; sulfolan; hexamethyl phosphoric acid triamide; dimethyl sulfoxide; ethylene glycol monomethyl ether acetate; di-n-propyl carbonate; cyclohexyl acetate; diisobutyl carbonate; diethylene glycol monomethyl ether acetate; d-isoamyl carbonate; 2-ethyl pyridine; N,N-dimethyl-2-methyl aniline; N,N-dimethyl aniline; N-methyl-N-ethyl aniline; N,N-dimethyl-2-chloroaniline; N,N-diethyl aniline; quinoline; nitrocyclohexane; nitrobenzene; 2-nitrotoluene; 2,4-dimethyl-1-nitrobenzene; acetonitrile; N-capronitrile; benzonitrile; tolunitrile; diphenylether; tetramethylurea and phenyl acetonitrile. It is particularly preferred to use polar solvents and mixtures thereof. ε-caprolactam is a particularly suitable solvent.

In many cases, for example where a large excess of reactant alcohol is used, there is no need for such solvents to be used. In particular, there is no need to use such auxiliary solvents in the production of monourethanes, i.e., where a single N-monosubstituted or N,N'-disubstituted monourea is used as the reactant substituted urea.

To carry out the process according to the present invention, the above-described starting materials are generally heated to a temperature of 120°–350° C. for a period of from 1 to 15 hours, preferably from 2 to 12 hours. The ammonia formed during the reaction must be permitted to escape.

In cases where the reactant alcohol does not correspond to the alcohol chemically bound in the reactant unsubstituted urethane and, optionally, in the substituted urea, it is necessary that the bound alcohol have a lower boiling point than the reactant alcohol so that the bound alcohol may be displaced by the reactant alcohol if uniform products are to be obtained. This displacement of the bound alcohol by the reactant alcohol generally takes place at the same time as the reaction forming the N,O-disubstituted urethane. However, the alcohol displacement may also be carried out beforehand, for example by initially heating the N-unsubstituted urethane with or part of the reactant alcohol to a suitable temperature lying within the above-mentioned ranges and distilling off the alcohol with the lower boiling point. The process of the present invention may then be carried out after addition of the remaining starting materials. In cases where N-unsubstituted urethanes containing an optionally chlorine- or $C_1$-$C_4$ alkyl-substituted phenol having a total of 6 to 15 carbon atoms as the O-substituent are used, a corresponding displacement reaction would also take place if the phenol formed were not removed from the mixture.

The products obtained by the process according to the present invention may be treated to remove starting materials and/or catalysts present by techniques known to those in the art. For example, readily volatile constituents (solvents and/or readily volatile, superfluous starting materials) may be distilled off. Insoluble constituents (for example, insoluble catalysts) may be filtered off before such distillation. After such treatment, the products may be used without further purification. This means that the process products may be thermally split into the isocyanate and the alcohol on which they are based immediately by techniques known to those in the art.

Having thus described our invention, the following Examples are given by way of illustration. The percentages quoted in these Examples represent percentages by weight unless indicated otherwise.

EXAMPLES

Example 1

A packed steel column (nominal width 50 mm) having a coil condenser as the head condenser was filled to a level of about 1 meter with rings (4 mm) of steel wire mesh cloth. Above the head condenser was a valve for removing gases. The sump vessel of the column was a steel pressure reaction vessel (nominal capacity, 5 liters; maximum permitted pressure, 64 bars) equipped with a stirrer and a heating jacket.

594 g of N,N'-diphenyl urea and 2075 g of n-butanol were introduced into the pressure vessel. The pressure vessel and the column were then purged with nitrogen and closed. The mixture was heated with stirring for 2 hours to 190° C. and then cooled again. 168 g of urea were then added to the pressure vessel and the mixture was reheated with stirring. By adjusting the valve at the head of the column and the cooling of the head condenser, the pressure prevailing in the apparatus was regulated in such a way that the required reaction temperature was reached. The mixture was heated to 200° C. and maintained for 5.5 hours. The ammonia given off during the reaction was freed from covolatilizing substances by rectification in the column and removed in the form of a substantially pure gas at the head of the column.

On completion of the reaction, the reaction mixture is cooled and, after venting of the apparatus, was removed therefrom. The solution was analyzed by high pressure liquid chromatography. A yield of 831 g of N-phenyl carbamic acid-n-butyl ester was determined, corresponding to 77% of the theoretical yield.

Example 2

Following the procedure of Example 1, 573 g of N,N'-diphenyl urea and 2080 g of ethanol (approximately 96%) were reacted for 1.5 hours at 190° C. in the pressure apparatus described in Example 1. After cooling this mixture, 162 g of urea and 5.8 g of zinc octoate were added to the pressure reactor and then reacted for 5.5 hours at 200° C. with removal of the ammonia formed. After cooling and venting of the apparatus, the reaction mixture was removed, filtered and subjected to fractional distillation. Excess alcohol was separated from the reaction mixture at atmospheric pressure. 783 g (87.8% of the theoretical yield) of N-phenyl carbamic acid ethyl ester distilled off at 0.2 mbar. The N-phenyl carbamic acid ethyl ester crystals melted at 49° to 51° C.

Example 3

637 g of N,N'-diphenyl urea, 267 g of ethyl carbamate and 1880 g of ethanol (approximately 96%) were reacted for 8.5 hours at 200° C. in the pressure apparatus described in Example 1, with the ammonia gas given off being removed. After cooling and venting of the apparatus, the reaction mixture was removed, filtered and subjected to fractional distillation. Excess alcohol was initially distilled off at atmospheric pressure, after which the mixture was distilled off at 0.2 mbar. 766 g (77.3% of the theoretical yield) of N-phenyl carbamic acid ethyl ester which solidified into crystals melting at from 48° to 51° C. were produced.

Example 4

673 g of N,N'-di-(3-methyl phenyl)-urea, 147 g of methyl carbamate, 475 g of methanol and 1500 g of o-xylene were reacted for 2 hours at 200° C. in the pressure apparatus described in Example 1, the ammonia given off being removed. After cooling, 50 g of urea were added to the mixture which was then reacted for 6.0 hours at 200° C., with removal of the formed ammonia given off. After cooling and venting of the apparatus, the mixture was removed, filtered and analyzed by liquid chromatography (HPLC). After calibration with an authentic sample, a yield of 660 g (71% of the theoretical yield) of N-(3-methyl phenyl)-carbamic acid methyl ester was determined.

Example 5

524 g of a polyurea mixture of 2,4-diaminotoluene containing terminal aminotolyl groups (average molecular weight, 1500) were introduced into the pressure apparatus described in Example 1. 352 g of ethyl carbamate, 1200 g of ethanol (approximately 96%), 900 g of o-xylene and 5.2 g of zinc octoate were then added. The mixture was stirred and reacted for 6.5 hours at 200° C., with removal of the ammonia given off. After cooling and venting of the apparatus, the reaction mixture was removed, filtered and analyzed by liquid chromatography (HPLC). A yield of 716 g (75% of the theoretical yield) of 2,4-bis-(ethoxy carbonylamino)-toluene was obtained.

Example 6

299 g of a polyurea mixture of 4,4'-diaminodiphenylmethane containing terminal 4-(p-aminobenzyl)-phenyl groups (average molecular weight, 1140) are introduced into the pressure apparatus described in Example 1, followed by the addition of 167 g of isopropyl carbamate, 393 g of isopropanol and 230 g of o-dichlorobenzene. The mixture was reacted for 8.5 hours at 200° C., with removal of the ammonia given off and then cooled. After venting of the apparatus, the reaction mixture was removed, filtered and analyzed by high pressure liquid chromatography. A yield of 340 g (68% of the theoretical yield) of 4,4'-bis-(isopropoxy carbonylamino)-diphenylmethane was determined.

Example 7

88 g of N,N'-dimethyl urea (1 mol), 60 g of urea (1 mol), 250 g of cyclohexanol (2.5 mols) and 3 ml of zinc octoate were mixed and heated to 145° C. The temperature was increased to 195° C. over a period of 5 hours and maintained for another 2 hours.

On completion of the reaction, excess cyclohexanol was distilled off, the residue was distilled in an oil pump vacuum and the reaction products were identified by IR and NR. 245 g of N-methyl-O-cyclohexyl urethane (78% of the theoretical yield) were produced.

Example 8

71.2 g of carbamic acid ethyl ester (0.8 mol), 171.6 g of the following compound:

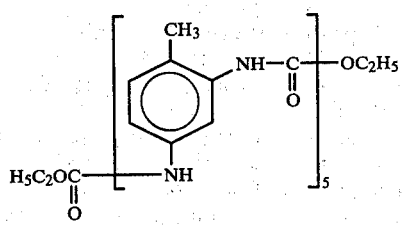

(0.2 mol), 280 g of cyclohexanol (2.8 mols) and 5 ml of zinc octoate were heated to reflux. Only a little $NH_3$ was given off. After the addition of 113 g of caprolactam (1 mol), the evolution of $NH_3$ and elimination of alcohol began at 160° C. The internal temperature was increased to 200° C. over a period of 3 hours and maintained for 10 hours.

The caprolactam and the cyclohexanol present in the product were then distilled off at 0.26 mbar.

Analysis of IR and NMR spectra showed that the residue consisted of 2,4-bis-(cyclohexoxy carbonylamino)-toluene, 254 g of the urethane (68% of the theoretical yield) were produced.

Example 9

2 ml of zinc octoate were added to 64 g of the following compound:

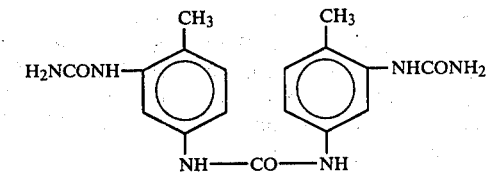

(0.18 mol), 10.8 g of urea (0.18 mol), 100 g of cyclohexanol and 113 g of caprolactam (1 mol). The mixture was heated to 200° C. and maintained at that temperature for 3 hours by which time the evolution of $NH_3$ ceased. After cooling, caprolactam and unreacted cyclohexanol were distilled off at 0.26 mbar. The residue was identified by IR and KR and a sample was recrystallized. 109 g of 2,4-bis-(cyclohexoxy carbonylamino)-toluene (81% of the theoretical yield) having a melting point of 155°–156° C. (from toluene) were produced.

Example 10

2 g of zinc acetate were added to 89 g of carbamic acid ethyl ester (1 mol), 196 g of N,N'-(3,3'-di-dibenzofuranyl)-urea (0.5 mol), 195 g of 2-ethyl-n-hexanol (1.5 mols). 100 g of caprolactam were then added as a solvent. The reaction was heated for 3 hours at 200° C. The ammonia and the ethyl alcohol formed were removed through a steam-heated condenser. The reaction mixture was then heated at 200° C. for another 6 hours. On completion of the reaction, caprolactam and residual 2-ethyl-n-hexanol were distilled off in an oil pump vacuum.

The residue was boiled with ethanol, cooled and filtered from the insoluble constituents. The filtrate was then concentrated. The thus-obtained residue was identified by IR and KR. 244 g of N-(3-dibenzofuranyl)-O-(2-ethyl hexyl)-urethane (72% of the theoretical yield) were produced.

Example 11

105 g of N,N'-diisobutyl urea (0.6 mol), 37 g of urea (0.6 mol) and 160 g of cyclohexanol (1.6 mols) were heated for 4 hours to 200° C. in the presence of 3 g of cobalt naphthanate and then maintained at that temperature for another 3 hours, by which time the evolution of ammonia was over.

The cyclohexanol still present in the residue was removed in a water jet vacuum, the major quantity being distilled in a high vacuum. 222 g of N-isobutyl-O-cyclohexyl urethane (93% of the theoretical yield) having a boiling point of 98°–102° C. at 0.4 mbar were produced.

Example 12

200.6 of N,N'-dihexyl urea (0.88 mol), 43 g of urea (0.88 mol) and 210 g of cyclohexanol (2.1 mols) were mixed with 3 g of zinc cyanide and the resulting mixture was heated to 150° C., thereby initiating the evolution of $NH_3$. The internal temperature was increased to 200° C. and maintained for 4 hours. Cyclohexanol was distilled off at 15 mbar and the residue fractionated in an oil pump vacuum. 368 g of N-(n-hexyl)-O-cyclohexyl urethane (92% of the theoretical yield) having a boiling point of 123°–125° C. at 0.06 mbar were produced.

Example 13

3 ml of zinc octoate were added to 202 g of N,N'-dicyclohexyl urea (0.9 mol), 55 g of urea (0.9 mol) and 180 g of cyclohexanol (1.8 mols) and the mixture was heated for 3 hours at 200° C. After 3 hours at that temperature, the evolution of $NH_3$ stopped and the reaction was terminated. The residue was then distilled. 415 g of N-cyclohexyl-O-cyclohexyl urethane (84% of the theoretical yield) having a boiling point of 142°–145° C. at 0.13 mbar were produced.

Example 14

30 g (0.5 mol) of urea, 106 g (0.5 mol) of N,N'-diphenyl urea, 305 g (2.5 mols) of β-phenyl ethanol and 1 g of zinc cyanide were heated under reflux for 4 hours. The yield of N-phenyl-O-β-phenyl ethyl urethane was determined by high pressure liquid chromatography and amounted to 92% of the theoretical yield. 212 g (88% of the theoretical yield) of the urethane were isolated by fractional distillation. The product crystals had a melting point of 78° C.

Example 15

106 g (1 mol) of N,N'-diphenyl urea, 300 g (3 mols) of cyclohexanol, 51.5 g (0.5 mol) of biuret and 0.7 g of zinc octoate were heated under reflux for 10 hours. The yield of N-phenyl-O-cyclohexyl urethane was determined by high pressure liquid chromatography and amounted to 96% of the theoretical yield.

Example 16

106 g (0.5 mol) of diphenyl urea, 50 g (0.5 mol) of cyclohexanol and 71.5 g (0.5 mol) of carbamic acid cyclohexyl ester were heated under reflux for 4 hours with 0.8 g of zinc octoate. The temperature rose to 200° C. during the reaction. Following the addition of another 0.3 mol of cyclohexanol, the temperature was maintained at 200° C. for another 5 hours. Analysis by high pressure liquid chromatography showed that N-phenyl-O-cyclohexyl urethane had formed in an amount which was 80% of the theoretical yield.

Example 17

424 g (2 mols) of N,N'-diphenyl urea and 120 g (2 mols) of urea were stirred for 12 hours at reflux in 800 g (8 mols) of cyclohexanol. The cyclohexanol was distilled off and the residue recrystallized from cleaning spirit. N-phenyl-O-cyclohexyl urethane melting at from 74° to 76° C. was obtained in a yield of 90% of the theoretical yield.

The reaction was repeated using 1 g of nickel chloride and 600 g (6 mols) of cyclohexanol, i.e., less alcohol. After a reaction time of 8 hours, the yield of O-cyclohexyl-N-phenyl urethane amounted to 91% of the theoretical yield.

Example 18

60 g (1 mol) of urea, 106 g (0.5 mol) of N,N'-diphenyl urea, 68 g (0.5 mol) of carbamic acid phenyl ester and 300 g (3 mols) of cyclohexanol were heated under reflux. The condenser was heated to 90° C. so that the ethanol formed was continuously distilled off. After 4 hours, the temperature had reached 200° C. and was maintained at that level for another 6 hours. The reaction product was then concentrated in a high vacuum (0.2 Torr, 120° C.) and the residue analyzed by high pressure liquid chromatography. N-phenyl-O-cyclohexyl urethane had formed in a yield of 93% of the theoretical yield.

Example 19

600 g (6 mols) of cyclohexanol were introduced at from 150° to 160° C. into a 2-liter, three-necked flask equipped with a stirrer, contact thermometer and reflux condenser. 392 g (2 mols of urea groups) of a polyurea which had been synthesized by reacting 1-amino-3,3,5-trimethyl-5-aminomethyl cyclohexane with urea in dichlorobenzene (average molecular weight approximately 1200) were then introduced in portions over a period of 2 hours. After cooling to 120° C., 120 g (2 mols) of urea and 5 g of copper acetate were added. The temperature was gradually increased to 210° C. over a period of 6 hours, during which 100 g (1 mol) of cyclohexanol were distilled off. 3.8 mols of ammonia (95% of the theoretical amount) were given off.

Excess and unreacted cyclohexanol were then distilled off in vacuo, leaving 820 g of a yellow resin of which 76% was found by high pressure liquid chromatography to consist of 1-(cyclohexoxy carbonylamino)-3,3,5-trimethyl-5-(cyclohexoxy carbonylaminoethyl)-cyclohexane. The yield was 74% of the theoretical yield.

What is claimed is:

1. A process for the preparation of N,O-disubstituted urethanes by reacting (a) substituted ureas with (b) alcohols at temperatures of from 120° to 350° C., characterized in that (c) N-unsubstituted urethanes and/or (d) urea and/or polyurets are used as further reactants in a quantity of at least 10% by weight, based on the quantity of substituted urea and the reaction is carried out in the presence of no more than 5% by weight, based on the sum of starting materials, of esterification catalysts for carboxylic acids.

2. The process of claim 1 in which the substituted ureas (a) are N,N'-disubstituted ureas.

3. The process of claim 1 in which the substituted ureas (a) are linear polyureas.

4. The process of claim 1, characterized in that the reaction is carried out in the presence of a polar solvent.

5. The process of claim 4, characterized in that the reaction is carried out in the presence of ε-caprolactam as solvent.

* * * * *